(12) United States Patent
Gharat et al.

(10) Patent No.: US 12,014,285 B2
(45) Date of Patent: Jun. 18, 2024

(54) SYSTEMS AND METHODS FOR MACHINE LEARNING IN PATIENT PLACEMENT

(71) Applicant: TeleTracking Technologies, Inc., Pittsburgh, PA (US)

(72) Inventors: Tejashree Vivek Gharat, Pittsburgh, PA (US); Srinivas Manoj Kamavarapu, McDonald, PA (US); Ratna Divya Kanthi Bejjam, Bridgeville, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 568 days.

(21) Appl. No.: 16/730,011

(22) Filed: Dec. 30, 2019

(65) Prior Publication Data

US 2020/0210868 A1 Jul. 2, 2020

Related U.S. Application Data

(60) Provisional application No. 62/786,781, filed on Dec. 31, 2018.

(51) Int. Cl.
| | |
|---|---|
| *G06N 5/04* | (2023.01) |
| *G06N 20/00* | (2019.01) |
| *G16H 10/60* | (2018.01) |
| *G16H 40/20* | (2018.01) |

(52) U.S. Cl.
CPC ............... *G06N 5/04* (2013.01); *G06N 20/00* (2019.01); *G16H 10/60* (2018.01); *G16H 40/20* (2018.01)

(58) Field of Classification Search
CPC ................................ G06N 20/00; G16H 10/60
See application file for complete search history.

(56) References Cited

U.S. PATENT DOCUMENTS

| | | | |
|---|---|---|---|
| 2009/0198733 A1 | 8/2009 | Gounares et al. | |
| 2013/0304512 A1* | 11/2013 | Seshadri ............... | G16H 40/67 705/3 |

(Continued)

OTHER PUBLICATIONS

Adrien Badre, "Secure Decentralized Decisions in Consolidated Hospital Systems: Intelligent Agents and Blockchain", A Thesis Submitted to the Graduate Faculty, University of Oklahoma Graduate College, Jan. 1, 2018, 56 pages, Copy Available at: https://shareok.org/bitstream/handle/11244/316289/2018_Badre_Adrien_Thesis.pdf?sequence=4&isAllowed=y.

*Primary Examiner* — Nicholas P Celani
(74) *Attorney, Agent, or Firm* — FERENCE & ASSOCIATES LLC

(57) ABSTRACT

The present disclosure relates to systems and methods for determining one or more appropriate treatment facilities for patient placement. A machine learning system may perform operations. The operations may receive a patient data set including patient attributes and patient location metrics; access a plurality of data sets for a plurality of medical facilities, the plurality of data sets include facility capacity, location, and capability metrics for each of the plurality of medical facilities; apply a model to match the patient data set with at least one of the plurality of medical facility data sets based on at least one of the patient attributes and patient location metrics and at least one of the facility capacity, location, and capability metrics; determine, based on the application of the model, one or more likelihoods of acceptance associated with each match.

17 Claims, 13 Drawing Sheets

(56) References Cited

U.S. PATENT DOCUMENTS

| | | | | |
|---|---|---|---|---|
| 2015/0363568 A1* | 12/2015 | Milo | ............... | G16H 50/30 |
| | | | | 705/2 |
| 2016/0012192 A1* | 1/2016 | Radhakrishnan | ...... | G16H 10/60 |
| | | | | 706/12 |
| 2017/0235898 A1* | 8/2017 | Coulter | ............ | G16H 40/20 |
| | | | | 705/2 |
| 2018/0052967 A1* | 2/2018 | Boomershine | ......... | G16H 20/00 |
| 2020/0066397 A1* | 2/2020 | Rai | ............ | G06Q 10/067 |

* cited by examiner

300

| Patient | Communication | Outcome | Documents |

Caller Information

Caller 1
Name*  [          ]
Phone# [        ] Ext. [    ]
☐ Caller 1 has been notified that the call is being recorded Caller 2
Name*  [          ]
Phone# [        ] Ext. [    ]
☐ Caller 2 has been notified that the call is being recorded

Referring Information

Referring Facility
Facility  [Begin typing and select from list]
Unit      [Begin typing and select from list]
Bed#      [        ]

Referring Physician
Name      [Begin typing and select from list]
🔍 Search for new physician
Phone #   [        ] Ext. [    ]
Diagnosis
Primary   [Begin typing and select from list]
Secondary [Begin typing and select from list]
Protocol  [        ]
☐ Patient qualifies for automatic acceptance.

Reason for Transfer
Reason    [Begin typing and select from list]

Requested Service
Speciality [Begin typing and select from list]
Procedure  [Begin typing and select from list]
☐ The referring facility offers this service.

Destination Details
Preferred    [Begin typing and select from list]
Destination  [Begin typing and select from list]

Case Type
Type      [Begin typing and select from list]

*FIG. 3A*

Basic Information 310

Patient Details
Last Name *
First Name *
Middle     Suffix
DOB
Gender *   ○ Male  ○ Female  ○ Unknown
Patient Type  [Begin typing and select from list]
⊕ Add home address information

Patient Identifiers
SSN
MRN
Visit No.
🔍 Check for Existing Patient

Infection Prevention
Has the patient (or someone they have been in contact with) travelled outside of the U.S. within the last 21 days?
○ Yes  ○ No

Primary Care Physician
Name   [Begin typing and select from list]
🔍 Search for new physician
Phone #            Ext.

Payor Information
Primary    [Begin typing and select from list]
Secondary  [Begin typing and select from list]
Tertiary   [Begin typing and select from list]

*FIG. 3B*

Clinical Details 320

Demographics
Weight [ ] lb    Height [ ]    OFC [ ]
        [ ] kg
Vital Signs  ⊕ Add vital signs

| | BP | HR | RR | SPO2 | Temp. |
|---|---|---|---|---|---|
| Date/Time 12/17/2018 [📅] 3:51 PM [Now] | [ ] | [ ] | [ ] | [ ] | [ ] |

Onset of Symptoms
Date/Time [📅] [HH:MM] [Now]

Treatment
1  [Begin typing and select from list]
Details [Begin typing and select from list]
⊕ Add another treatment

Medication / Drips
1  [Begin typing and select from list]
Dosage [ ]
Time [ ]
⊕ Add another medication

Isolation
ISO Type  [Begin typing and select from list]
Organisms [Begin typing and/or select from list]

Alerts
Medical Alerts [Begin typing and/or select from list]

Allergies
Known Allergies [Begin typing and/or select from list]

Patient Code Status
Status [Begin typing and select from list]

*FIG. 3C*

Referrals
Create Referral

| Access | On call | Analytics | Admin |

Welcome, administrator | Sign Out

Patient AdmissionDetails
Patients referred from:
All My Facilities

| Anderson, Iggy | PreAdmit |
METHODIST
Assign Bed
H.1093A
Admitting Physician
--
Patient waiting to be admitted.

| A, Aaron | PreAdmit |
≉ METHODIST
Assign Bed
--
Admitting Physician
--
Patient waiting to be admitted.

| new3, test3 | PreAdmit |
STONE OAK
Assign Bed
--
Admitting Physician
--
Patient waiting to be admitted.

| TestDefect1030 | PreAdmit |
TEXSAN1
Assign Bed

SSN [ - - ]

Clinical Summary

Clinical Details

Diagnosis [Begin typing and select from list]

Isolation* [Begin typing and select from list]

Level of Care* [Begin typing and select from list]

Clinical Notes

[                    ]

255 characters remaining.

Referral Information

Referring Facility

Requester* [          ]

Phone # [          ]

Referring Physician* [Begin typing and select from list]

Facility Name* [Begin typing and select from list]

Preferred Facility

Facility Name* [Begin typing and select from list]

Admitting Physician [Begin typing and select from list]

ETA

Date/Time* [06/06/2018] [4:01 AM] [Now]

[Submit Referral] [Cancel]

SYSTEMS AND METHODS FOR MACHINE LEARNING IN PATIENT PLACEMENT

PRIORITY CLAIM

This application claims priority from U.S. Provisional Application No. 62/786,781 filed Dec. 31, 2018, which is hereby incorporated by reference in its entirety.

TECHNICAL FIELD

The present disclosure relates generally to the field of machine learning systems. More specifically, and without limitation, this disclosure relates to systems and methods for determining one or more appropriate treatment facilities for patient placement using improved applications of machine learning technology.

BACKGROUND

Modern medical facilities often operate in networks having multiple buildings within a geographical region. However, current systems for placing patients are disparate and individualized for each building. Patient's commonly are transferred between medical facilities, but the transfer process suffers multiple drawbacks due to the disparate current systems. Patient transfer often involves a referring facility calling a number of other facilities, or a call center that communicates with other facilities, in order to determine a destination facility for the patient. This process is manual, time consuming, and may involve the use of simple rule sets. Because the process for selecting a transferee facility is largely manual and relies on human workflow, the process is subject to error, inefficiency, and a gross lack of optimization of facility resources, resulting in inefficient or ineffective patient transfer. Current systems that assist the human actors in the transfer process rely on simple statistic calculations but lack the ability to analyze complex scenarios and evaluate multiple facilities in real time, further hindering the transfer process.

In view of these drawbacks of current systems, improvements in computer systems for transferring patients between facilities are desired.

SUMMARY

In view of the foregoing, embodiments of the present disclosure describe systems and methods for systems and methods for determining one or more appropriate treatment facilities for patient placement. The provided systems may use machine learning systems and methods to determine one or more appropriate treatment facilities for patient placement.

In one embodiment, the present disclosure describes a machine learning system for determining one or more appropriate treatment facilities for patient placement. The machine learning system may include at least one memory storing instructions, and at least one processor configured to execute the instructions to perform operations. The operations may include receive a patient data set comprising patient attributes and patient location metrics; access a plurality of data sets for a plurality of medical facilities, the plurality of data sets comprising facility capacity metrics, facility location metrics, and facility capabilities for each of the plurality of medical facilities; apply a model to match the patient data set with at least one of the plurality of medical facility data sets based on at least one of the patient attributes and patient location metrics and at least one of the facility capacity metrics, facility location metrics, and facility capabilities; determine, based on the application of the model, one or more likelihoods of acceptance associated with each match; output the at least one match with the associated likelihoods to a user device.

In another embodiment, a method for determining one or more appropriate treatment facilities for patient placement. The method may include the following steps performed by at least one processor: storing, in a database, a plurality of data sets for a plurality of medical facilities, the plurality of data sets comprising facility capacity metrics, facility location metrics, and facility capabilities for each of the plurality of medical facilities; storing, in the database, a patient data set comprising patient attributes and patient location metrics; extracting the patient data set; applying a model to match the patient data set with at least one of the plurality of medical facility data sets based on at least one of the patient attributes and patient location metrics and at least one of the facility capacity metrics, facility location metrics, and facility capabilities; determining, based on the application of the model, one or more likelihoods of acceptance associated with each match; and displaying the at least one match with the associated likelihoods to a user device.

In another embodiment, the present disclosure describes a non-transitory, computer-readable medium storing instructions that, when executed by at least one processor, cause the at least one processor to perform operations, the operations including: generating a user interface displaying a plurality of graphics each being selectable. The plurality of graphics may include: a text box for entry of a location a name of a medical facility; a visual indicator that displays a capacity of the medical facility; a visual indicator that displays a distance from a patient to the medical facility; a visual indicator displaying a likelihood the medical facility will accept the patient; a selector for the medical facility; assembling the user interface; transmitting the user interface to a display.

It is to be understood that the foregoing general description and the following detailed description are example and explanatory only and are not restrictive of the disclosed embodiments.

BRIEF DESCRIPTION OF THE DRAWINGS

The accompanying drawings, which comprise a part of this specification, illustrate several embodiments and, together with the description, serve to explain the principles disclosed herein. In the drawings:

FIG. 3A is an example graphical user interface for acquiring data about a patient to be supplied to a machine learning system, according to an example embodiment of the present disclosure.

FIG. 3B is an example graphical user interface for acquiring data about a patient to be supplied to a machine learning system, according to an example embodiment of the present disclosure.

FIG. 3C is example another graphical user interface for acquiring data about a patient to be supplied to a machine learning system, according to an example embodiment of the present disclosure.

FIG. 4 is another example graphical user interface for acquiring data about a patient to be supplied to a machine learning system, according to an example embodiment of the present disclosure.

DETAILED DESCRIPTION

The disclosed embodiments relate to systems and methods for determining one or more appropriate treatment facilities for patient placement. Embodiments of the present disclosure may be implemented using a general-purpose computer programmed with special purpose machine learning software configured to perform one or more operations disclosed herein. Alternatively, a special-purpose computer may be built according to embodiments of the present disclosure using suitable logic elements.

According to an aspect of the present disclosure, one or more servers or other computing devices may store data relating to patients in a hospital or other medical campus or network and data relating to medical facilities. The servers or computing devices may include at least one memory storing instructions, and at least one processor configured to execute the instructions to perform operations as described below. For example, data may be stored and indexed based on patient attributes and facility attributes, as will be discussed in more detail below.

The servers may receive, from a user device, a request to access data from a database. For example, the user may include a caregiver (such as a doctor, nurse, surgeon, or the like) and may send the request using a user interface device such as a smartphone, tablet, laptop, or the like. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the servers may decrypt the request using a private key. Similarly, in embodiments where any of the requested data is encrypted, the servers may decrypt during the extraction of the data.

The database may include patient-specific and/or facility-specific data and/or may include aggregated data. In some embodiments, the aggregated data may have been converted from a database to an object in an object-oriented programming language. For example, the servers may perform one or more join commands on the data to generate an object in an object-oriented programming language having the joined data. The join commands may be in an appropriate relational database language such as SQL.

Figure 1:
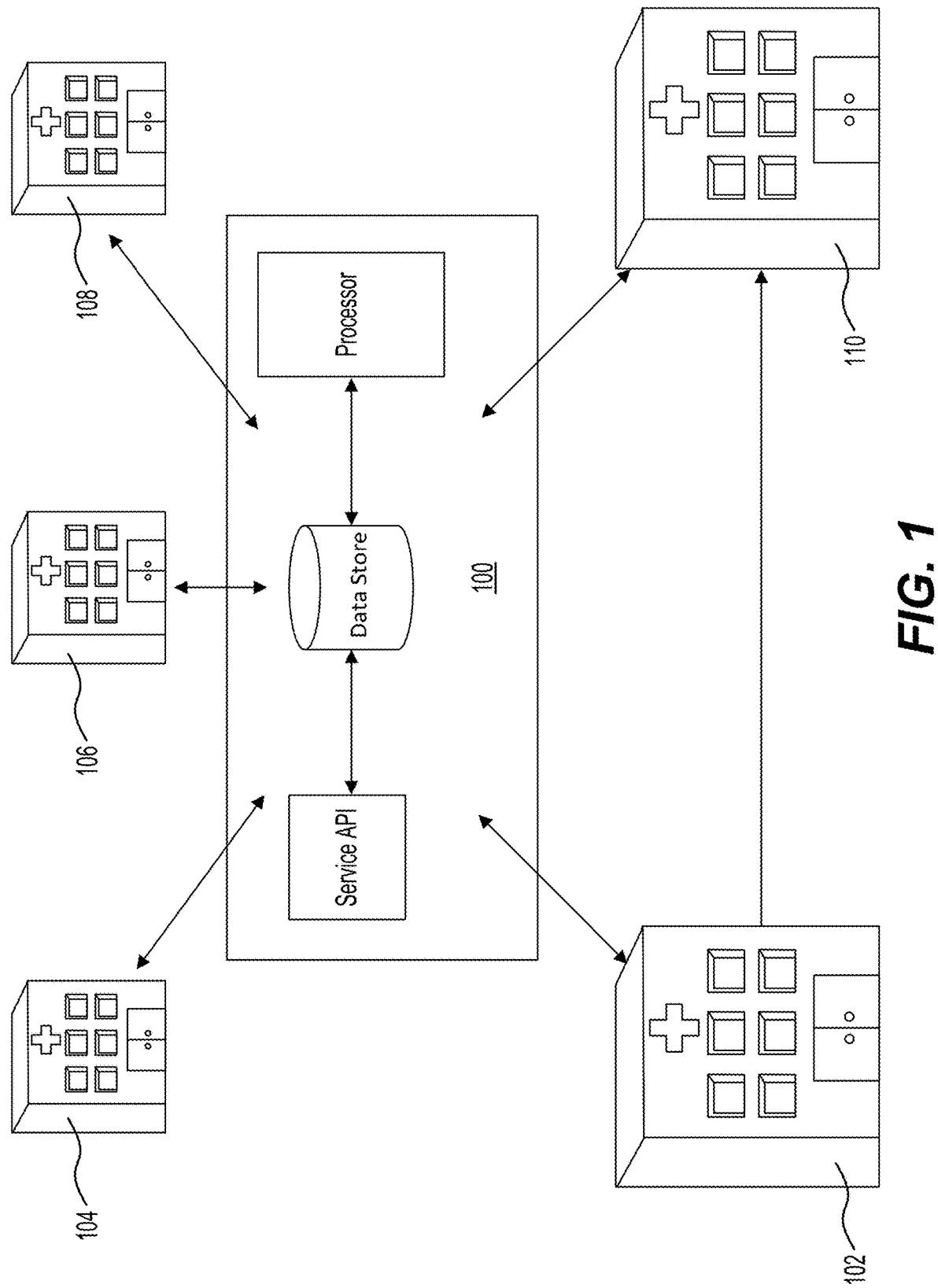
FIG. 1 is a schematic diagram of a machine learning system for determining one or more appropriate treatment facilities for patient placement, according to an example embodiment of the present disclosure.

FIG. 1 shows a schematic diagram of a machine learning system 100 for determining one or more appropriate treatment facilities for patient placement, according to an example embodiment of the present disclosure. The machine learning system 100 may be in communication with a number of treatment facilities (e.g. 102, 104, 106, 108, 110). The number of treatment facilities shown is exemplary and not intended to be limited to the specific number of facilities illustrated. A patient may be located at a referring facility 102, but the referring facility 102 may not be an appropriate facility for the patient for a number of reasons. Some examples include, but are not limited to: insufficient capacity, excessive wait time, insufficient level of care, inability to provide a patient treatment, lack of necessary specialists, insurance not supported, transportation not available, new incoming patient, physician unavailable, among others. As a result, the patient may need to visit another facility that meets the requirements of the patient's treatment protocol. The patient may have a number of options (e.g. facilities 104, 106, 108, 110) in determining another facility to be transferred to. The referring facility 102 may be in communication with the machine learning system 100 and may communicate a patient data set to the machine learning system.

The patient data set data set can include information about the patient indicative of the patient's need and required facility attributes to associate an appropriate facility with the patient. In some embodiments, the patient data set may include patient attributes and patient location metrics. Patient attributes may include, but are not limited to: patient weight, patient's address state, patient's requested bed type, patient's diagnosis, emergency medical condition (EMC) status, illness history, oxygen needed, oxygen rate, isolation indication, level of care, patient age, patient sex, patient type, payor (insurance), procedure requested, service requested, transfer reason, medication drips required, systolic blood pressure, diastolic blood pressure, heart rate, heart rhythm, respiratory rate, patient temperature, pulse oximetry (oxygen saturation in patient's blood), case entry month, case entry day, case entry week, case entry day of year, case entry hour, case entry week day, among others.

Facilities 102, 104, 106, 108, 110 may be in communication with the machine learning system 100 and may communicate facility-specific data to the machine learning system 100. The facility-specific data sets may include real-time facility capacity metrics, facility location metrics, and facility capabilities for each of the plurality of medical facilities (e.g. 102, 104, 106, 108, 110). The plurality of data sets for medical facilities 102, 104, 106, 108, 110 may further include prior entries of similar patients, data showing similarities in facilities, and data showing differences in facilities. Additionally, the facility-specific data may include an internal transportation mode offered from referring to transfer facility, the referring physician, the referring unit, and a list of offered services that can be matched with the requested service offered at referring facility 102 or the other facilities 104, 106, 108, 110.

Additional data may be supplied to the machine learning system 100 by one or more networked third party systems (not shown in figures), including, but not limited to: weather data, schedule information for major events like sports, music concerts, disasters, natural calamities, crimes, air quality and street traffic information, holidays, and transport schedules and delays (for medical transports, public transportation, or private transportation services) in the area of the referring facility 102 or the other facilities 104, 106, 108, 110.

Based on the request, the servers of the machine learning system 100 may extract the patient-specific data and the facility-specific data from the database. For example, the servers may generate one or more commands in an appropriate database language such as SQL to extract the data.

Once the extracted data is stored as one or more objects, the servers may convert the object to a data serialized format configured for use in a graphical user interface generator. For example, the objects may be converted to a JavaScript Object Notation (JSON) file, an Extensible Markup Language (XML) file, or the like. Such files may allow for compatibility with web-based application programming interfaces (APIs). Accordingly, the request received from the user device may comprise an API pull of a data serialized format.

In alternate embodiments, the servers may store the patient-specific and/or facility-specific data in a NoSQL database, such as MongoDB. In such embodiments, the request received from the user device may comprise a MongoDB pull, and the servers may directly extract the data serialized format from the MongoDB database based on the pull.

In embodiments where patient-specific data is requested and pulled, at least the portion of the request corresponding to the patient-specific data and/or at least the portion of the data serialized format corresponding to the patient-specific data may be encrypted. This may retain the privacy of medical data.

As depicted in FIG. 1, the machine learning system 100 may have a service API that can receive requests for information. In some embodiments, the service API may be a mobile service API. The service API may receive unencrypted and/or encrypted requests. In some embodiments, the service API may require connection to a private network (and/or to a virtual private network (VPN)) for requests to be received. This may, for example, allow for aggregated data and requests to remain unencrypted without significant risk of interception.

The service API may authenticate the user on a content management system (CMS) server and/or a cloud web service (CWS) server. Such authentication may verify that the user has the credentials to view requested data. Additionally, the CMS server and/or CWS sever may confirm that a role of the user is permitted to view the requested data. For example, a request from an executive to view patient-specific data may be denied by the CMS server and/or CWS server Advantageously, disclosed embodiments may provide for secure and confidential pulls from medical databases. Accordingly, the database pulls may be adjusted based on user input and on user roles to ensure the most useful data is pulled and that the pulls are compliant with privacy concerns.

The machine learning system 100 may store a computer model or a plurality of computer models that, when applied to the patient-specific data and facility specific data, matches the patient data set with at least one of the plurality of medical facility data sets based on at least one of the patient attributes and patient location metrics and at least one of the facility capacity metrics, facility location metrics, and facility capabilities.

The model may be continuously improved when encountered with additional patient-specific data and facility-specific data. Additionally, the model may have previously been exposed to an abundance of patient-specific data and facility-specific data training the machine learning system 100 and the associated model to match the patient data set with at least one of the plurality of medical facility data sets. The model may have been trained by supplying training data sets, validation data sets, and testing data sets. For example, the model may have been created using the training data sets and machine learning algorithms. The generated model may be built using a neural network.

The machine learning system 100 may determine, based on the application of the model, one or more likelihoods of acceptance associated with each match. Likelihoods of acceptance may be associated with the facilities 104, 106, 108, 110 likelihood to accept the patient based on the patient-specific data and the facility-specific data. More specifically, the likelihoods of acceptance may be associated with the capacity of the facility, the distance from the patient, and the facility attributes, such as services provided. Likelihoods of acceptance can also be based on prior entries of similar patients, utilizing the model's continuous improvement capabilities to update likelihoods of acceptance at facilities 104, 106, 108, 110 in real time, ultimately leading to one of the facilities (e.g. destination facility 110) being chosen. In some embodiments, each patient and facility attribute may be assigned a score or weight that may be based on the training data that was provided to the machine learning system 100, as will be discussed in further detail below. When new records (e.g. patient specific data and facility specific data) are given to the trained model, the model will output a probability of Acceptance or Decline.

In some embodiments, the servers or other computing devices may aggregate patient-specific and/or medical facility-specific data into one or more statistics. For example, a facility capacity based on a total number of available beds, a total number of occupied beds, a total number of patients, or the like may be calculated. Additional statistics may be derived from various aggregations. For example, the servers may calculate a ratio or percentage of available beds, a ratio or percentage of patients awaiting care to patients receiving care, or the like. The statistics may also be aggregated based on locations (e.g., average wait time by campus, percentage of available beds by building, percentage of patients by category such as radiology or geriatrics, or the like), may be aggregated based on statuses (e.g., percentage of vacant beds, percentage of vacant beds that are clean, or the like).

In some embodiments, the data may be encrypted. Alternatively, the aggregated statistics may be stored in an unencrypted format to increase speed of access without violating privacy concerns.

The machine learning system 100 may output the at least one match with the associated likelihoods to a user device, and a GUI may be rendered reflecting this output, as will be discussed below.

Figure 2:
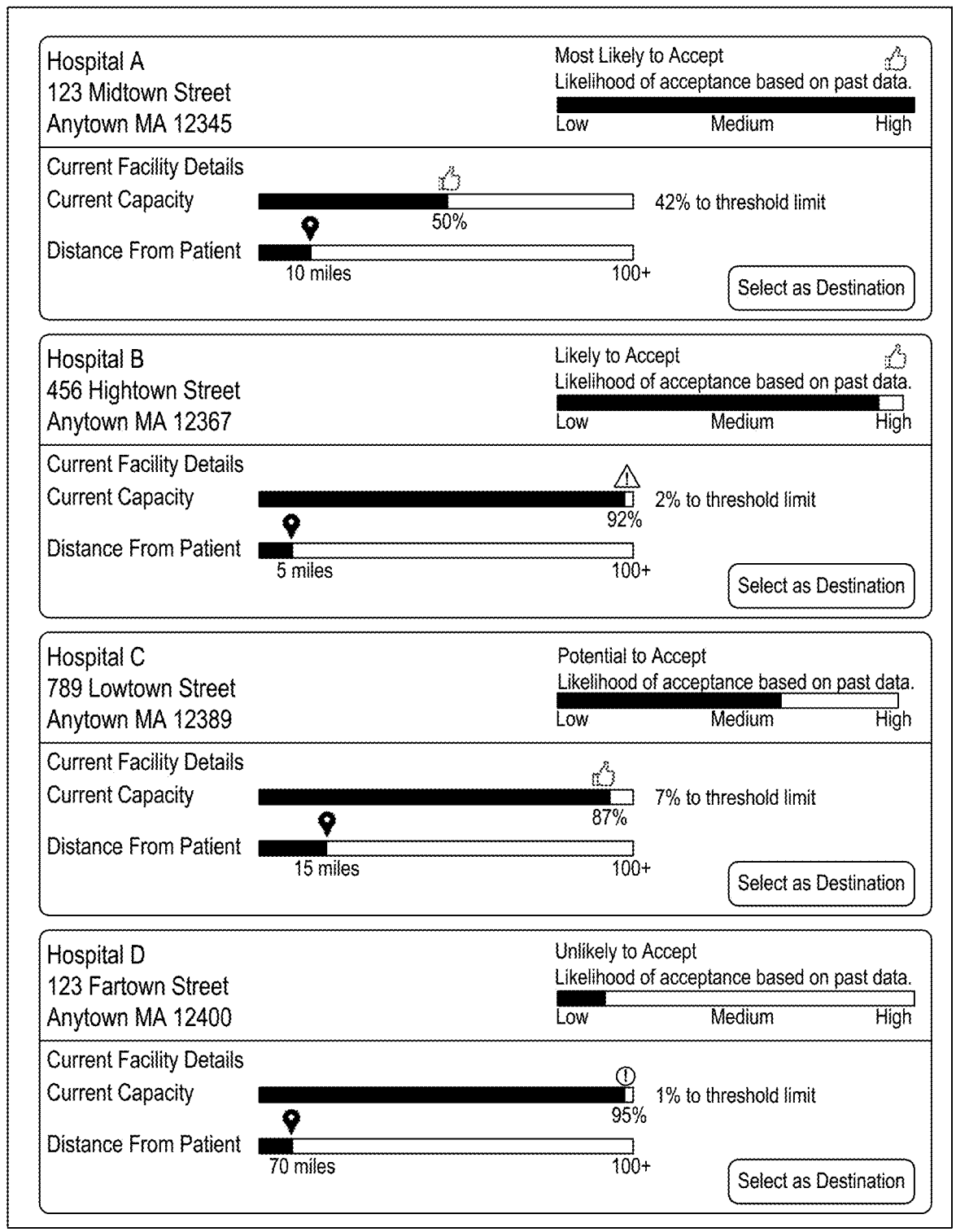
FIG. 2 is an example graphical user interface for visualizing data from a machine learning system, according to an example embodiment of the present disclosure.

FIG. 2 depicts a graphical user interface 200 for visualizing data from the machine learning system 100. Interface 200 may be generated for display on a screen of a user interface device (e.g., screen 1601 of FIG. 8). In the example of FIG. 2, visual indicators for plurality of facilities are shown in separate text boxes. Each facility may display a plurality of visual indicators associated with the facility and the patient. For example, the interface 200 may include a text box for entry of a location a name of a medical facility. The location and name of the medical facility may be auto-filled into the text box based on the facility-specific data received from the machine learning system 100.

The interface 200 may also include a visual indicator that displays a capacity of the medical facility. The visual indicator may be a bar, a chart, a wheel, or any other visual indicator suitable for displaying the capacity of the facility. The capacity may be displayed in percentage form, where the percentage represents the percentage of the facility's capacity to a threshold capacity where the facility becomes less likely to accept patients. In a non-limiting example, the threshold may be set by the facility based on the number of available beds as discussed above. The capacity may be tracked and displayed in real-time to ensure the patient receives updated information about the capacity of the facility.

Another visual indicator may display a graphical representation of a distance from a patient to the medical facility. The visual indicator may be a bar, a chart, a wheel, a map, or any other visual indicator suitable for displaying the distance from the patient to the facility. Another visual indicator may be a likelihood of acceptance visual indicator, as discussed above. The likelihood of acceptance indicator may be a bar, a chart, a wheel, or any other visual indicator suitable for displaying the likelihood of acceptance for the facility to accept the patient. The likelihood of acceptance visual indicator may include multiple thresholds delineating between how likely the facility may be to accept the patient. For example, the visual indicator may include a low threshold, a medium threshold, and a high threshold showing the likelihood of acceptance for the patient.

The interface 200 may also include a selector for the medical facility. The selector may be a push button or selectable area of the user interface associated with a specific facility and the selector may allow a user to choose a facility based on the graphical indicators and suggestions provided in the displayed graphical user interface, such as the indicated likelihood of acceptance.

The interface 200 may include the visual indicators discussed above for a plurality of facilities. For example, the interface 200 may include the visual indicators discussed above for two or more facilities, allowing the user to decide between the two or more facilities based on the visual indicators of the interface 200. In some embodiments, the displayed visual indicators may be grouped by facility, and the facilities may be ranked according to metrics such as a distance from the patient, or the likelihood of acceptance. Additionally, a "thumbs-up" visual indicator may indicate an output from the machine learning system 100 that reflects a suggested match for the patient to be directed to a facility or not. The "thumbs-up" indicator may also reflect a current capacity below a threshold, the threshold indicating a likelihood that the specific facility still has sufficient remaining capacity to accept the patient. A "thumbs-down" visual indicator may indicate an output from the machine learning system 100 that reflects a suggested mismatch or where the machine learning system 100 suggests a patient should not be directed to a facility. Warning visual indicators may also be present as exclamation marks within a triangle to indicate a warning for a particular indicator (e.g. current capacity). Additionally, a critical warning can be present with an exclamation mark in a circle to indicate a critical warning for a particular indicator (e.g. current capacity).

FIG. 3A depicts a graphical user interface 300 for visualizing a data form that collects data to be supplied to the machine learning system 100. The interface 300 may collect caller information about a number of callers, for example, a first caller and a second caller, and may collect the name of the caller and the phone number of the caller. The caller information may be collected in a series of text boxes.

The interface 300 may also include referring information about the referring facility, the referring physician, the diagnosis, the reason for transfer, the requested service, the destination details, and the case type in a series of text boxes. The referring facility information may include the name of the facility, the unit of the facility, and the bed number. The referring physician information may include the physician name and phone number. The diagnosis information may include the primary and secondary diagnoses, protocol, and a checkbox for a patient qualified for automatic acceptance. The requested service information may include specialty information, procedure information, and a checkbox for the referring facility offers this service. The destination details information may include a preferred destination, a destination, and a redirect reason.

FIG. 3B depicts a graphical user interface 310 for visualizing a data form that collects data to be supplied to the machine learning system 100. The interface 310 may collect patient information, for example, patient details and patient identifiers. The patient details may include the name of the patient, the date of birth ("DOB"), the gender, and the patient type. The patient identifiers may include the social security number "SSN", the medical record number ("MRN"), the visit number, and the ability to check for an existing patient, which may be a push button. The patient information may be collected in a series of text boxes.

The interface 310 may also include information about the primary care physician, the payor information, and infection prevention. The primary care physician name and phone number may be provided. The primary, secondary, and tertiary payor information may be entered. It may also be entered into a yes/no checkbox if the patient (or someone they have been in contact with) has travelled outside of the United States within a certain window of time (such as the last twenty-one (21) days). The primary care physician and payor information may be collected in a series of text boxes.

FIG. 3C depicts a graphical user interface 320 for visualizing a data form that collects data to be supplied to the machine learning system 100. The interface 320 may collect clinical details such as demographics, including weight, height, occipitofrontal circumference (OFC). The interface 320 may collect vital signs including date/time, blood pressure ("BP"), heart rate ("HR"), respiratory rate ("RR"), peripheral capillary oxygen saturation ("SpO2"), temperature, among others. The interface 320 may further include a date/time for the onset of symptoms, the type of treatment and details associated with that treatment (and any subsequent treatments), the type of medication or medications or drips along with the dosage and time, along with any subsequent or additional medications and drips. Additionally, the interface 320 may collect isolation type and organisms, allergies, medical alerts, and patient code status information. This information may be collected in a series of text boxes.

FIG. 4 depicts a graphical user interface 400 for visualizing a data form that collects data to be supplied to the machine learning system 100. The interface 400 may collect referral information. The interface 400 may have a text box for a social security number ("SSN"). The interface may further include a clinical summary having a diagnosis, an isolation indication, a level of care indication, and a section for clinical notes. The interface 400 may further include referral information including referring facility information such as the requestor, the phone number, the referring physician, and facility name. The preferred facility information may include the facility name, the admitting physician, and the estimated time of arrival.

Figure 5A:
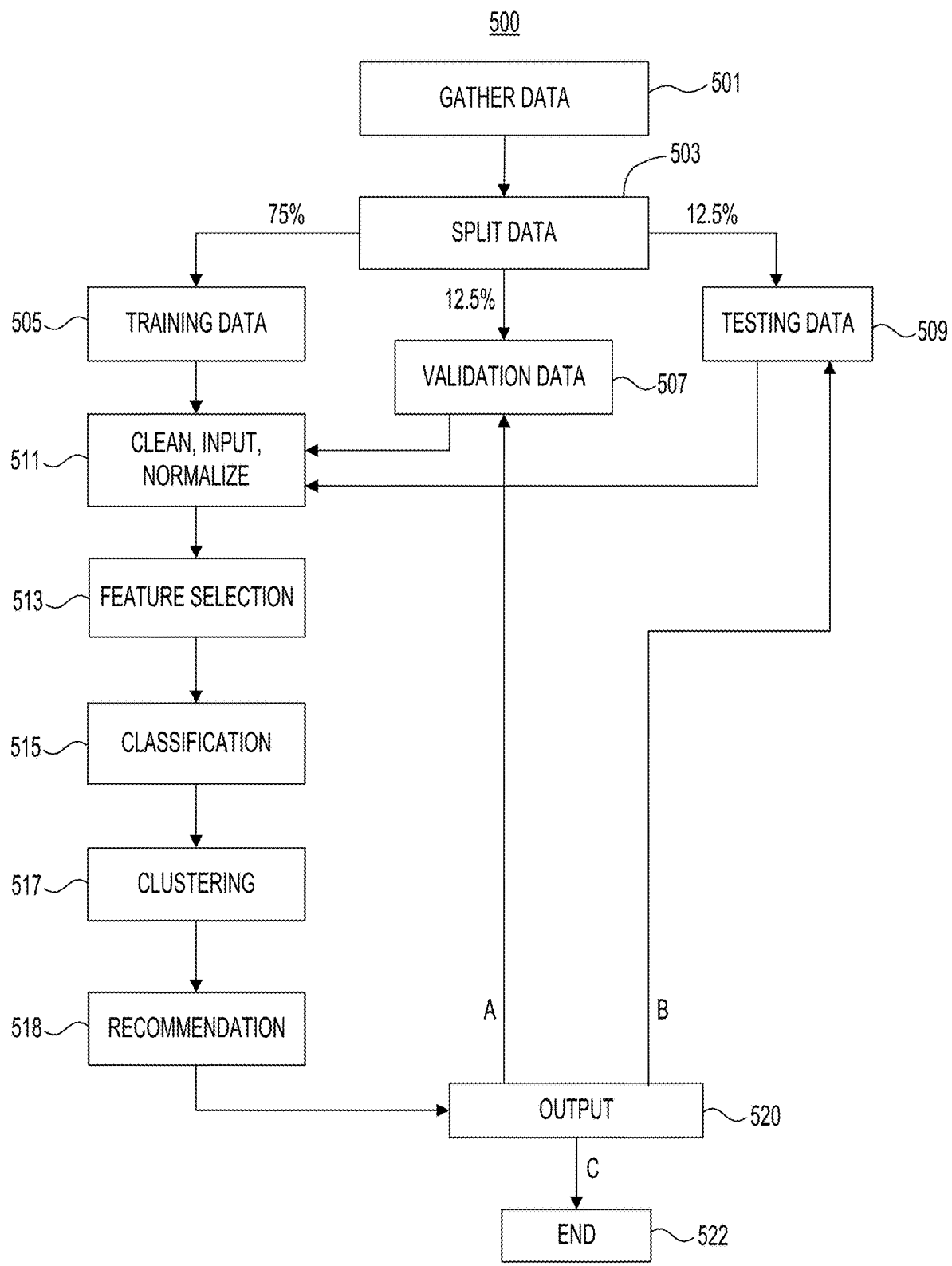
FIG. 5A is a flowchart of an example method for creating a machine learning model for determining one or more appropriate treatment facilities for patient placement, according to an exemplary embodiment of the present disclosure.

FIG. 5A depicts an example method 500 for creating a machine learning model. Method 500 may be implemented using one or more processors (e.g. processor 1503 of FIG. 7).

At step 501, data is gathered for training, validation and testing the machine learning model. The data may be gathered from archived sources where the data has been gathered over a number of years by an operational platform. At step 503, the data gathered at step 501 is split into training data 505, validation data 507, and testing data 509. In some embodiments, approximately 75% of the gathered data is split into training data 505 and approximately 12.5% of the gathered data is split into both the validation data 507 and the testing data 509.

At step 511, the training dataset is cleaned, imputed and normalized. At step 513, feature selection is performed using domain knowledge and algorithms that may be supervised (e.g. Linear Discriminant Analysis—LDA, etc.) or unsupervised (e.g. Principal Component Analysis—PCA, etc.). Feature selection may include selecting features such as the patient specific data and facility specific data discussed herein. Additionally, external or environmental features may be selected as well, including but not limited to: weather conditions, events/festivals in the surrounding regions, air quality, traffic, accidents, crimes, etc. Additionally, the physician that was contacted in the facility and their attributes such as whether they were an On-call or consulting physician, how many times in the past have they accepted, declined or just consulted the incoming patient on the basis of similarity in patients, and whether their role was an escalation role may be included in feature selection at step 513. In some embodiments, feature selection 513 may utilize algorithms such as dimensionality reduction, feature extraction, One Hot Encoding, Feature Hashing, Principal Component Analysis (PCA), Linear Discriminant Analysis (LDA), among others.

At step 515, the features selected at step 513 may undergo classification. The classes can be divided into a particular facility's acceptance or decline. Then the classification algorithm can be applied. The classification of features may utilize algorithms such as Naive Bayes, Tree Algorithms—Decision Trees, Random Forest, XGBoost Neural Networks Support Vector Machines, among others.

At step 517, the classified features may undergo clustering. Facilities may be clustered by computing similarity between them using their attributes and patient's attributes as features to the clustering algorithms. Patients may be clustered by computing similarity between them using their attributes and facilities' attributes as features to the clustering algorithms. Clusters are used for mapping patients to their appropriate set of facilities for a recommendation. The clustering of classified features may utilize algorithms such as K-means, Mean Shift Clustering, Density Based Spatial Clustering of Applications with noise (DBSCAN), Agglomerative Hierarchical clustering, among others.

At step 518, the clustered classified features may undergo recommendation. Similar patients may be recommended for admission to the same facility, and a patient may be recommended for admission to facilities having similar characteristics and capabilities. The recommendation step may utilize algorithms such as content based filtering and collaborative filtering, among others.

With such algorithms discussed herein regarding feature selection, classification, clustering, and recommendation, certain attributes are assigned weight or importance with the amount of data that represents such cases.

Following step 518, step 520 outputs the resulting trained machine learning model built based on the training data 505. After the model has been trained on the training data 505, the output 520 follows line A to undergo validation. The validation data 507 undergoes steps 511 through 518. The validation dataset may be used to tune hyperparameters to avoid overfitting and other data fallacies. The output 520 follows line C to test the trained and validated model. The testing data 509 undergoes steps 511 through 518.

After testing, the model may update continuously with each new case presented to the model. Multiple models may be created for different health systems. Once the model is created, it may be stored in the database that resides in a data platform and is used in an operational platform. The model may update itself using one or more known online learning techniques. Each time a case is created, the model may be applied to get a new prediction/recommendation. If the recommendation is not ideal, the model may retrain itself and capture the error. The model keeps retraining itself actively as and when new data comes in, and the model adjusts the predictions/recommendations accordingly in a cyclic process.

Figure 5B:
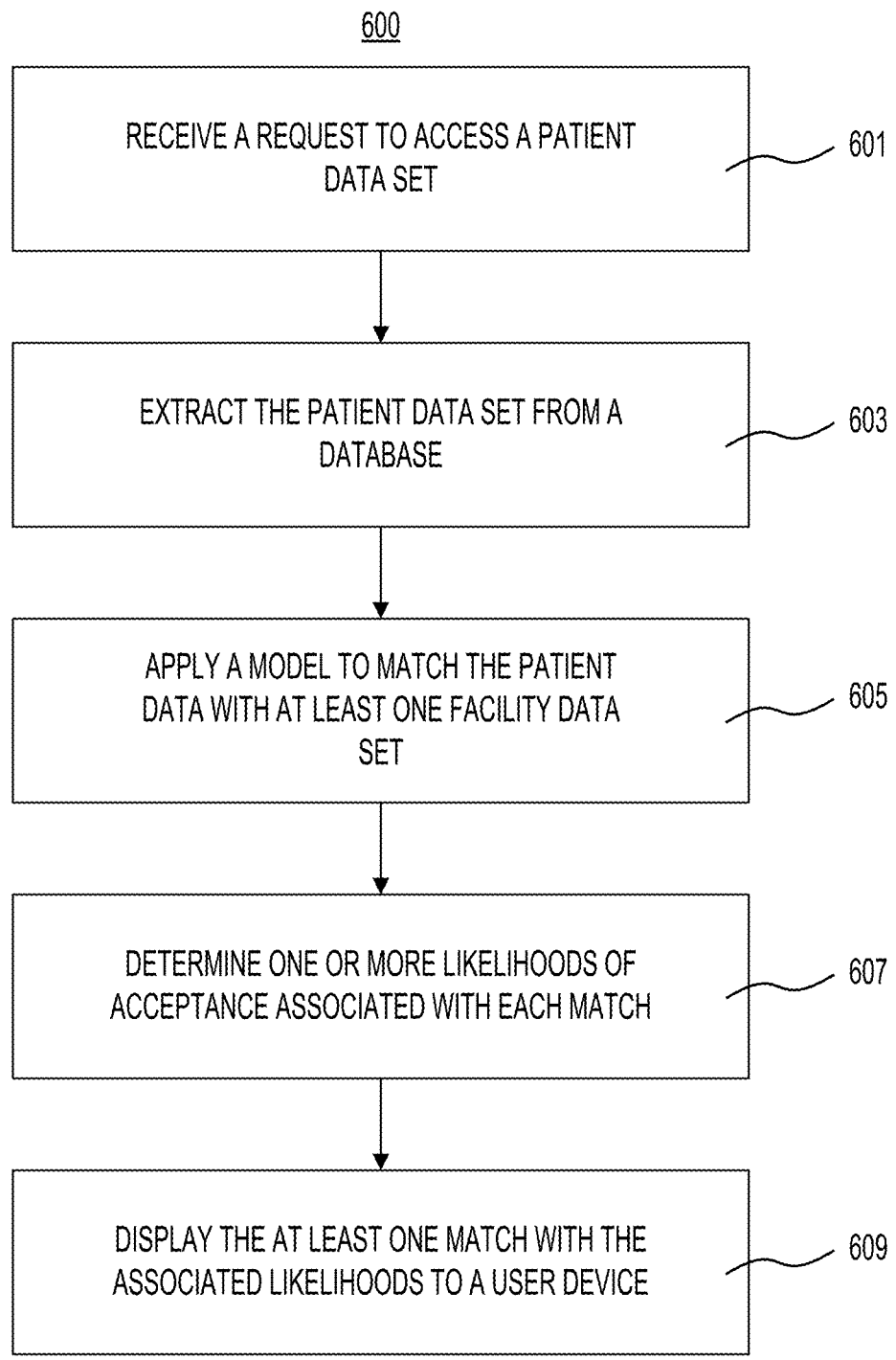
FIG. 5B is a flowchart of an example method for determining one or more appropriate treatment facilities for patient placement by applying a machine learning model, according to an example embodiment of the present disclosure.

FIG. 5B depicts an example method 600 for machine learning-based patient placement. Method 600 may be implemented using one or more processors (e.g., processor 1503 of FIG. 7).

At step 601, the processor may receive a request from a user to access a patient data set. For example, the user may comprise a caregiver (such as a doctor, nurse, surgeon, or the like) and may send the request using a user interface device. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the processor may decrypt the request using a private key. In some embodiments, the request received from the user device may comprise an API pull of a data serialized format.

The database may store patient-specific data in a hospital or other medical campus or network and facility-specific data, as discussed above. For example, data may be stored and indexed based on patient and/or based on beds. In some embodiments, the processor may aggregate patient-specific and/or bed-specific data into one or more statistics, as explained above.

At step 603, based on the request, the processor may extract the data from the database. For example, the servers may generate one or more commands in an appropriate relational database language such as SQL to extract the data. In embodiments where the aggregated data is stored as one or more objects, the servers may extract the aggregated data using an index or other matching technique to match the appropriate object(s) to the request. In some embodiments, the servers may perform one or more join commands on at least part of the extracted data (e.g., a part that is not already stored in an object) to generate an object in an object-oriented programming language having the joined data.

In some embodiments, at least a portion of the data in the database may be encrypted. In such embodiments, method 600 may further include decrypting the data during extraction.

At step 605, the processor may apply a model to match the patient data set with at least one of the plurality of medical facility data sets based on at least one of the patient attributes and patient location metrics and at least one of the facility capacity metrics, facility location metrics, and facility capabilities, as discussed above.

In some embodiments, the patient data set may include patient attributes and patient location metrics. Patient attributes may include, but are not limited to: patient weight, patient's address state, patient's requested bed type, patient's diagnosis, emergency medical condition (EMC) status, illness history, oxygen needed, oxygen rate, isolation indication, level of care, patient age, patient sex, patient type, payor (insurance), procedure requested, service requested, transfer reason, medication drips required, systolic blood pressure, diastolic blood pressure, heart rate, heart rhythm, respiratory rate, patient temperature, pulse oximetry (oxygen saturation in patient's blood), case entry month, case entry day, case entry week, case entry day of year, case entry hour, case entry week day, among others.

In some embodiments, the model may apply one hot encoding to some or all of the patient data set. In a non-limiting example, the patient sex may be encoded to be associated with a male, female, or unknown sex. Additionally, or in conjunction with one hot encoding, the model may utilize feature hashing to vectorize features in the patient specific data and facility specific data into a vector or matrix. Principle component analysis may also be used to reduce dimensions and may use an orthogonal transformation to convert a set of observations of possibly correlated variables into a set of values of linearly uncorrelated variables, or principle components. Additionally, or alternatively, a multilayer perceptron may be utilized, multilayer perceptron may use back-propagation as a feedforward artificial neural network.

At step 607, the processor may determine, based on the application of the model, one or more likelihoods of acceptance associated with each match, as discussed above. At step 609, displaying the at least one match with the associated likelihoods to a user device (e.g. screen 1601). At step 609, the processor may convert the object to a data serialized format configured for use in a graphical user interface generator. For example, the objects may be converted to a JavaScript Object Notation (JSON) file, an Extensible Markup Language (XML) file, or the like. Such files may allow for compatibility with web-based APIs.

The model may determine the likelihoods of acceptance based at least in part on facilities historical likelihood to accept the patient based on the patient-specific data and the facility-specific data. More specifically, the likelihoods of acceptance may be associated with the capacity of the facility, the distance from the patient, and the facility attributes, such as services provided. Likelihoods of acceptance can also be based on prior entries of similar patients, utilizing the model's continuous improvement capabilities to update likelihoods of acceptance at facilities in real time, ultimately leading to one of the facilities.

In some embodiments, Bayesian Learning may be implemented to compute posterior probability, also referred to as the probability of the hypothesis given the patient specific data and facility specific data.

The data serialized format may be configured for use in a graphical user interface generator. For example, the graphical user interface generator may generate any of the graphical user interfaces described and depicted above.

At step 609, the processor may transmit the data serialized format to the user device. For example, the servers may transmit the data serialized format over one or more computer networks, such as the Internet, a local area network (LAN), or the like, and may be sent using WiFi, 4G, Ethernet, or the like. In some embodiments, to retain security, the data serialized format may be sent over a private network (such as a LAN) and/or may be encrypted (e.g., using an Advanced Encryption Standard (AES)). In embodiments where the data serialized format is encrypted, the user interface device may decrypt the data serialized format, e.g., using a private key.

In some embodiments, method 600 may include additional steps that are not shown. For example, method 600 may further include encrypting at least a portion of the data serialized format. For example, the portion may correspond to any portion of the data including patient-specific data (such as personal health information (PHI)).

Figure 6:
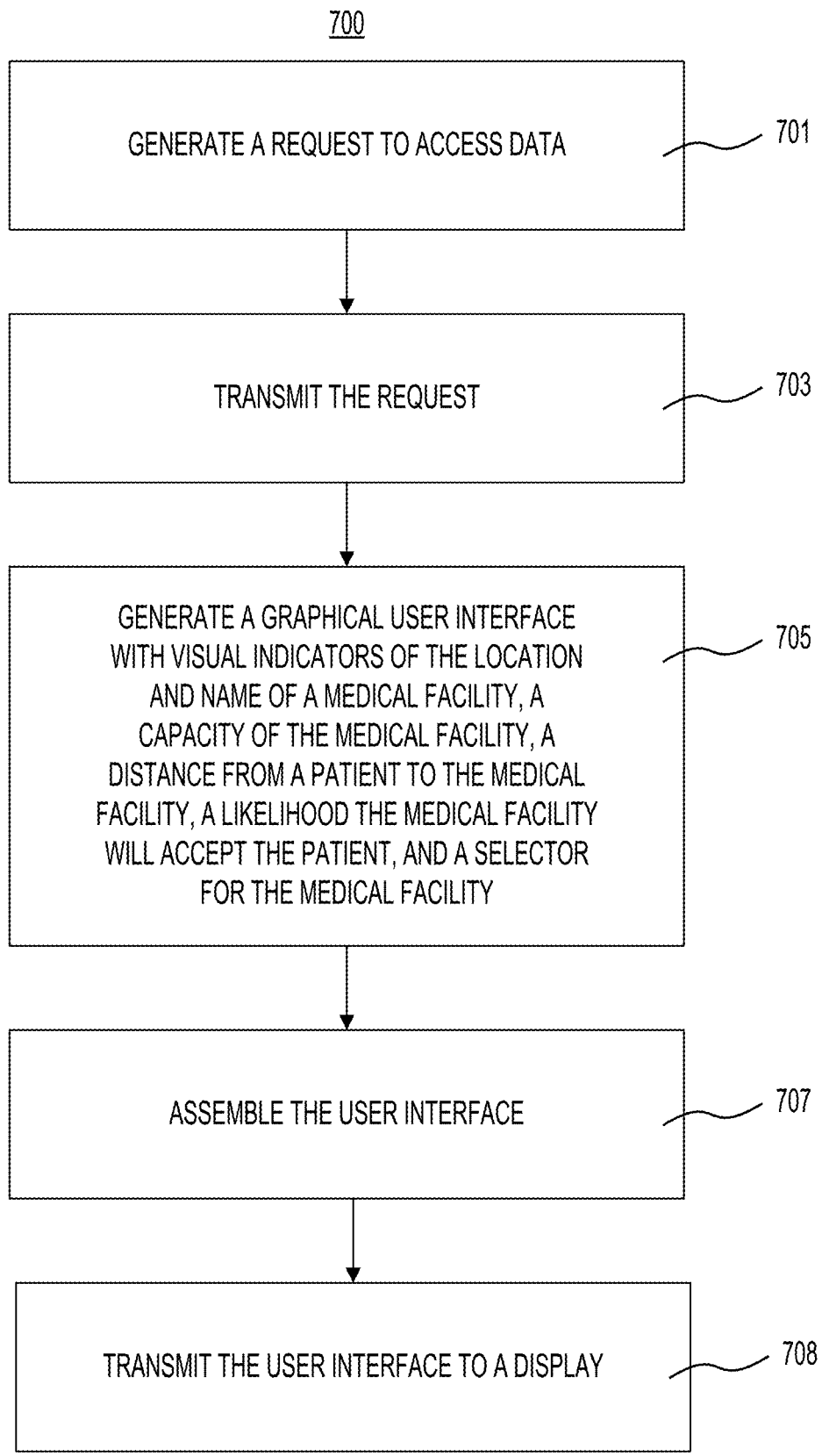
FIG. 6 is a flowchart of exemplary steps for generating a user interface displaying a plurality of graphics, according to an example embodiment of the present disclosure.

FIG. 6 illustrates a flowchart of exemplary method 700 for generating a user interface displaying a plurality of graphics, according to an example embodiment of the present disclosure. Method 700 may be implemented using one or more processors (e.g., processor 1503 of FIG. 7).

At step 701, the at least one processor may generate a request to access data and at step 703 the at least one processor may transmit the request, as described in reference to the method 600. At step 701, the processor may generate a request for data from a database. The data requested may be selected based on user input and based on a role of the user, as explained above.

At step 703, the processor may transmit the request to a remote device. For example, the user interface device may transmit the request over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the remote device may decrypt the request, e.g., using a private key.

At step 706, the processor may generate a user interface displaying a plurality of graphics each being selectable, the plurality of graphics including: a text box for entry of a location a name of a medical facility, a visual indicator that displays a capacity of the medical facility, a visual indicator that displays a distance from a patient to the medical facility, a visual indicator displaying a likelihood the medical facility will accept the patient, a selector for the medical facility, assembling the user interface, transmitting the user interface to a display. Examples of these visual indicators are discussed in reference to FIGS. 2-4.

At step 705, the processor may generate a graphical user interface including visual representations of the data in the data serialized format. For example, the customized graphical interfaces discussed above may be used to display the data. Graphical representations may include pie charts, bar graphs, and other visual representations of the received data. The graphical interfaces may also include text and numbers displaying the received data.

In some embodiments, the generated graphical user interface may be selected from a plurality of graphical user interfaces based on the requested data and based on the role.

For example, the processor may select from one of the disclosed graphical interfaces (or variations thereof) based on the received data and based on the role. The data serialized format may be configured for use in a graphical user interface generator. For example, the graphical user interface generator may be configured to select one of a plurality of graphical user interfaces customized based on a role of the user.

Figure 7:
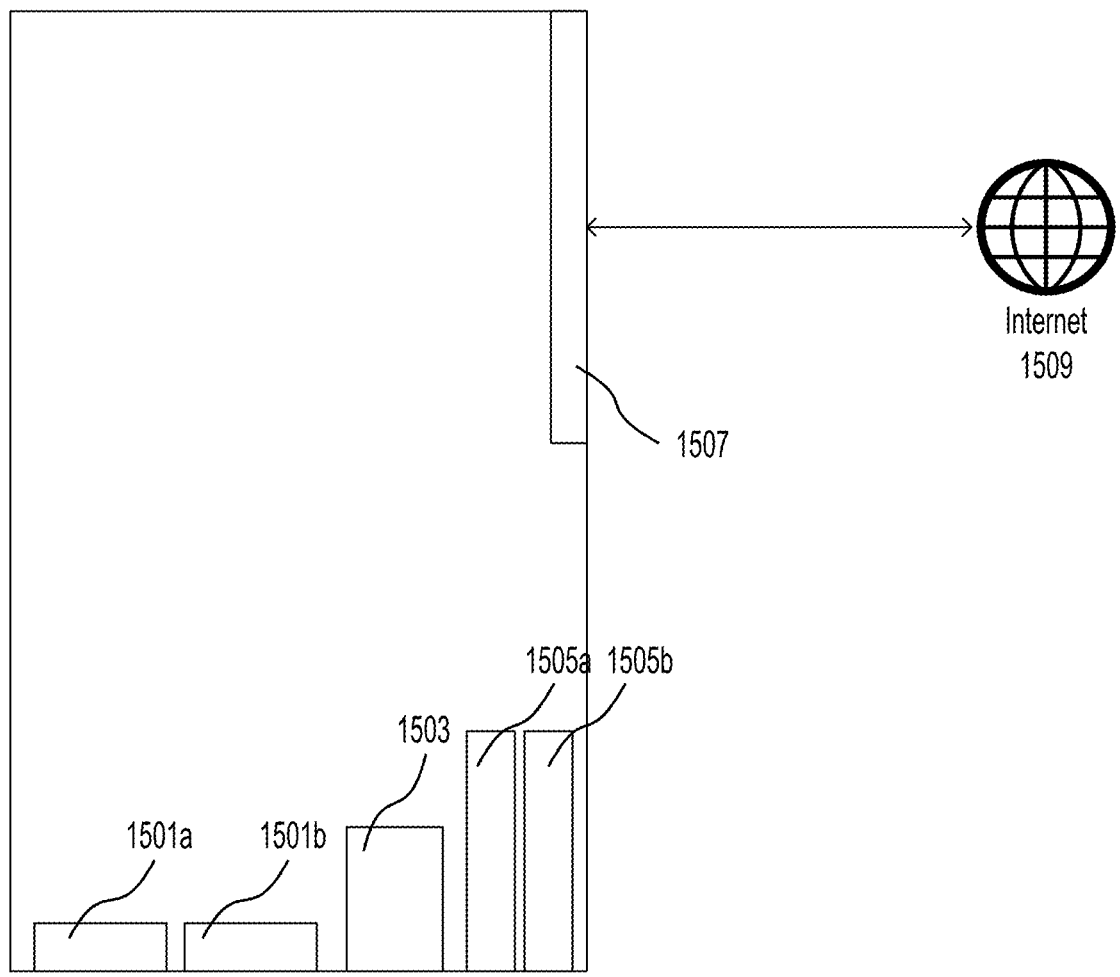
FIG. 7 is a block diagram of an example server with which the systems, methods, and apparatuses of the present invention may be implemented.

FIG. 7 is block diagram of an example server 1500 suitable for implementing the disclosed systems and methods. In some embodiments, server 1500 may comprise a server operating at one or more of the facilities discussed with respect to FIG. 1. In some embodiments, server 1500 may comprise multiple distributed components in a distributed computing system or a cloud computing system. In some embodiments, server 1500 may execute method 600 of FIG. 5. In some embodiments server 1500 may comprise a desktop computer, portable computer, smartphone, or tablet computer having sufficient computing power to perform operations disclosed herein.

As depicted in FIG. 7, example server 1500 may include at least one processor (e.g., processor 1503) and at least one memory (e.g., memories 1505a and 1505b).

Processor 1503 may comprise a central processing unit (CPU), a graphics processing unit (GPU), or other similar circuitry capable of performing one or more operations on a data stream. Processor 1503 may be configured to execute instructions that may, for example, be stored on one or more of memories 1505a and 1505b. Processor 1503 may comprise a single or multi-core processor, or a collection of separate processors that are networked or connected to perform distributed computing functions consistent with known distributed computing and cloud computing systems.

Memories 1505a and 1505b may be volatile memory (such as RAM or the like) and/or non-volatile memory (such as flash memory, a hard disk drive, or the like). As explained above, memories 1505a and 1505b may store instructions for execution by processor 1503.

As further depicted in FIG. 7, server 1500 may include at least one network interface controller (NIC) (e.g., NIC 1507). NIC 1507 may be configured to facilitate communication over at least one computing network (e.g., network 1509, which is depicted in the example of FIG. 7 as the Internet). Communication functions may thus be facilitated through one or more NICs, which may be wireless and/or wired and may include an Ethernet port, radio frequency receivers and transmitters, and/or optical (e.g., infrared) receivers and transmitters. The specific design and implementation of the one or more NICs depend on the computing network 1509 over which server 1500 is intended to operate. For example, in some embodiments, server 1500 may include one or more wireless and/or wired NICs designed to operate over a GSM network, a GPRS network, an EDGE network, a Wi-Fi or WiMax network, and a Bluetooth® network. Alternatively or concurrently, server 1500 may include one or more wireless and/or wired NICs designed to operate over a TCP/IP network.

As further depicted in FIG. 7, server 1500 may include and/or be operably connected to one or more storage devices, e.g., storages 1501a and 1501b. Storage devices 1501a and 1501b may be volatile (such as RAM or the like) or non-volatile (such as flash memory, a hard disk drive, or the like).

Processor 1503, memories 1505a and 1505b, NIC 1507, and/or storage devices 1501a and 1501b may comprise separate components or may be integrated in one or more integrated circuits. The various components in server 1500 may be coupled by one or more communication buses or signal lines (not shown).

In some embodiments, one or more sensor devices (not shown) may be provided in and around the facilities shown in FIG. 1. Such sensor devices may be used to collect real-time data about facility capacity, such as occupancy sensors. In some embodiments, sensors distributed in communities around the facilities may collect real-time data about traffic, weather hazards, and other factors that may affect the likelihood of acceptance for a given facility, or the ability to transfer a patient to a different facility.

Figure 8:
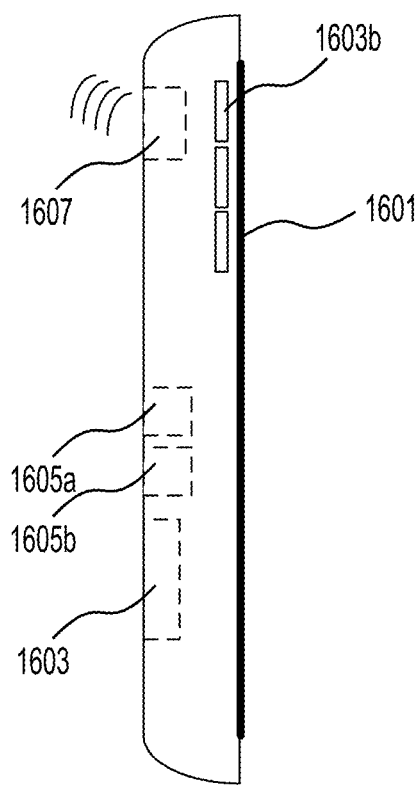
FIG. 8 is a block diagram of an example user interface device with which the systems, methods, and apparatuses of the present invention may be implemented.

FIG. 8 is block diagram of an example user interface device for implementing the disclosed systems and methods. Device 1600 may comprise a smartphone, tablet, or the like.

Device 1600 may have a screen 1601. For example, screen 1601 may display one or more graphical user interfaces (e.g., interfaces 200-500 of FIGS. 2-4) that visualize data from a secure database pull in a role-based application. In certain aspects, screen 1601 may comprise a touchscreen to facilitate use of the one or more GUIs.

As further depicted in FIG. 8, device 1600 may have at least one processor 1603. For example, at least one processor 1603 may comprise a system-on-a-chip (SOC) adapted for use in a portable device, such as device 1600. Alternatively or concurrently, at least one processor 1603 may comprise any other type(s) of processor.

As further depicted in FIG. 8, device 1600 may have one or more memories, e.g., memories 1605a and 1605b. In certain aspects, some of the one or more memories, e.g., memory 1605a, may comprise a volatile memory. In such aspects, memory 1605a, for example, may store one or more applications (or "apps") for execution on at least one processor 1603. For example, an app may include an operating system for device 1600 and/or an app for executing method 600 of FIG. 5. In addition, memory 1605a may store data generated by, associated with, or otherwise unrelated to an app in memory 1605a.

Alternatively or concurrently, some of the one or more memories, e.g., memory 1605b, may comprise a non-volatile memory. In such aspects, memory 1605b, for example, may store one or more applications (or "apps") for execution on at least one processor 1603. For example, as discussed above, an app may include an operating system for device 1600 and/or an app for executing method 1400 of FIG. 14. In addition, memory 1605b may store data generated by, associated with, or otherwise unrelated to an app in memory 1605b. Furthermore, memory 1605b may include a pagefile, swap partition, or other allocation of storage to allow for the use of memory 1605b as a substitute for a volatile memory if, for example, memory 1605a is full or nearing capacity.

As depicted in FIG. 8, device 1600 may include at least one network interface controller (NIC) (e.g., NIC 1607). NIC 1607 may be configured to facilitate communication over at least one computing network. Communication functions may thus be facilitated through one or more NICs. Although depicted in wireless in FIG. 8 and including radio frequency receivers and transmitters and/or optical (e.g., infrared) receivers and transmitters, NIC 1607 may alternatively be wired and include an Ethernet port or the like. The specific design and implementation of the one or more NICs depend on the computing network over which user interface device 1600 is intended to operate. For example, in some embodiments, user interface device 1600 may include one or more wireless and/or wired NICs designed to operate over a GSM network, a GPRS network, an EDGE network, a Wi-Fi or WiMax network, and a Bluetooth® network. Alternatively or concurrently, user interface device 1600 may include one or more wireless and/or wired NICs designed to operate over a TCP/IP network.

Each of the above identified instructions and applications may correspond to a set of instructions for performing one or more functions described above. These instructions need not be implemented as separate software programs, procedures, or modules. Disclosed memories may include additional instructions or fewer instructions. Furthermore, various functions of server 1500 and/or user interface device 1600 may be implemented in hardware and/or in software, including in one or more signal processing and/or application specific integrated circuits.

Figure 9:
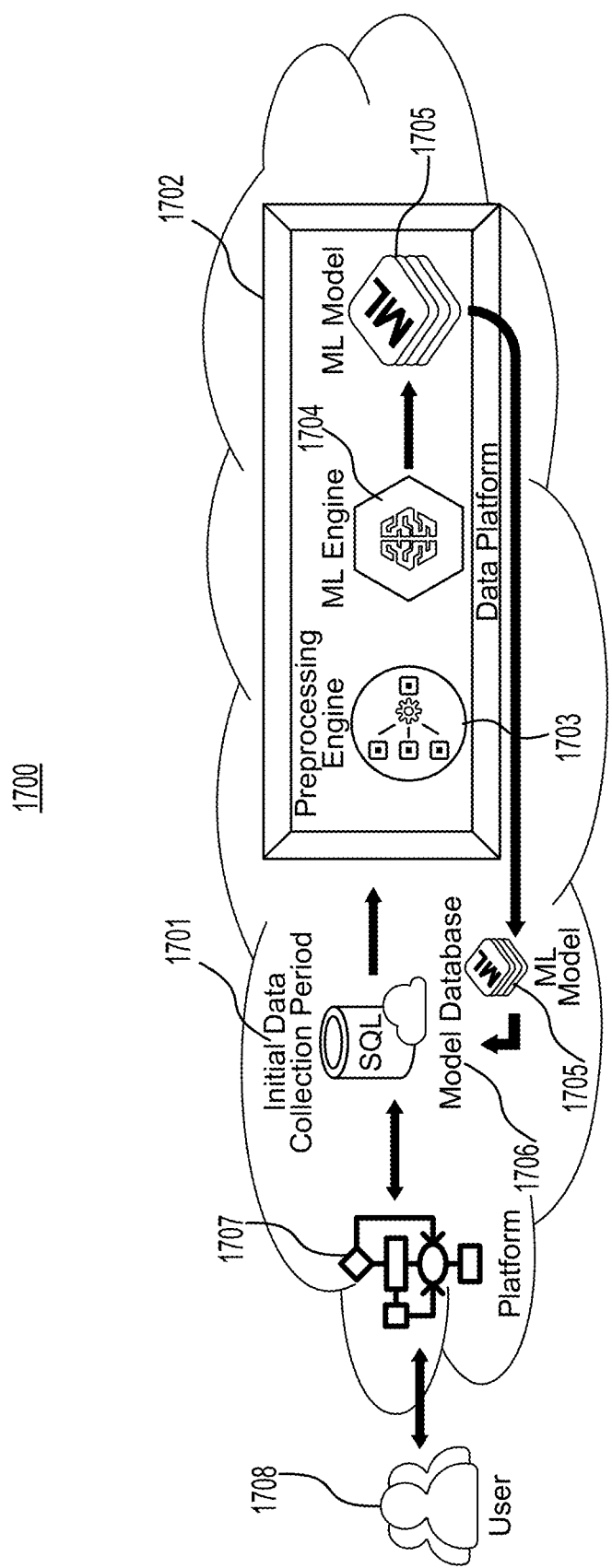
FIG. 9 is a schematic diagram of a machine learning system for determining one or more appropriate treatment facilities for patient placement, according to an example embodiment of the present disclosure.

FIG. 9 illustrates an exemplary machine learning system 1700 for determining one or more appropriate treatment facilities for patient placement, according to an exemplary embodiment of the present disclosure. Machine learning system 1700 may include an initial data collection period 1701 where a database collects data from previous patient specific data, facility specific data, and associated acceptance or rejection results. The initial data may be transmitted to a data platform 1702 where the initial data may undergo preprocessing via a preprocessing engine 1703. The preprocessed data may be transmitted from the preprocessing engine 1703 to a machine learning engine 1704 which may form, refine, and update a machine learning model 1705 based on the data provided to the machine learning engine 1704.

The machine learning model 1706 may determine, based on the application of the model to the data, one or more likelihoods of acceptance associated with matches of patient specific data with facility specific data, as discussed above. Likelihoods of acceptance may be associated with the facility's likelihood to accept the patient based on the patient-specific data and the facility-specific data. More specifically, the likelihoods of acceptance may be associated with the capacity of the facility, the distance from the patient, and the facility attributes, such as services provided. Likelihoods of acceptance can also be based on prior entries of similar patients, utilizing the model's continuous improvement capabilities to update likelihoods of acceptance at facilities The machine learning model 1705 may communicate with a model database 1706 that provides the data output from the machine learning model 1705 (e.g. matches between patient specific data and facility specific data and associated likelihoods of acceptance). The model database 1706 may form a database for additional data processing, that allows for continuous improvement of the machine learning model 1705. The model database 1706 may transmit the data provided by the model database 1706 to a platform 1707 that can communicate with a user 1708.

In some embodiments, the machine learning model 1705 may determine the appropriate facility for patient placement and may automate the placement of that patient. For example, instead of providing a recommendation of the facilities most likely to accept the patient, the machine learning model may automate the placement of the patient in the facility that model determined to be the best match for the patient.

Figure 10:
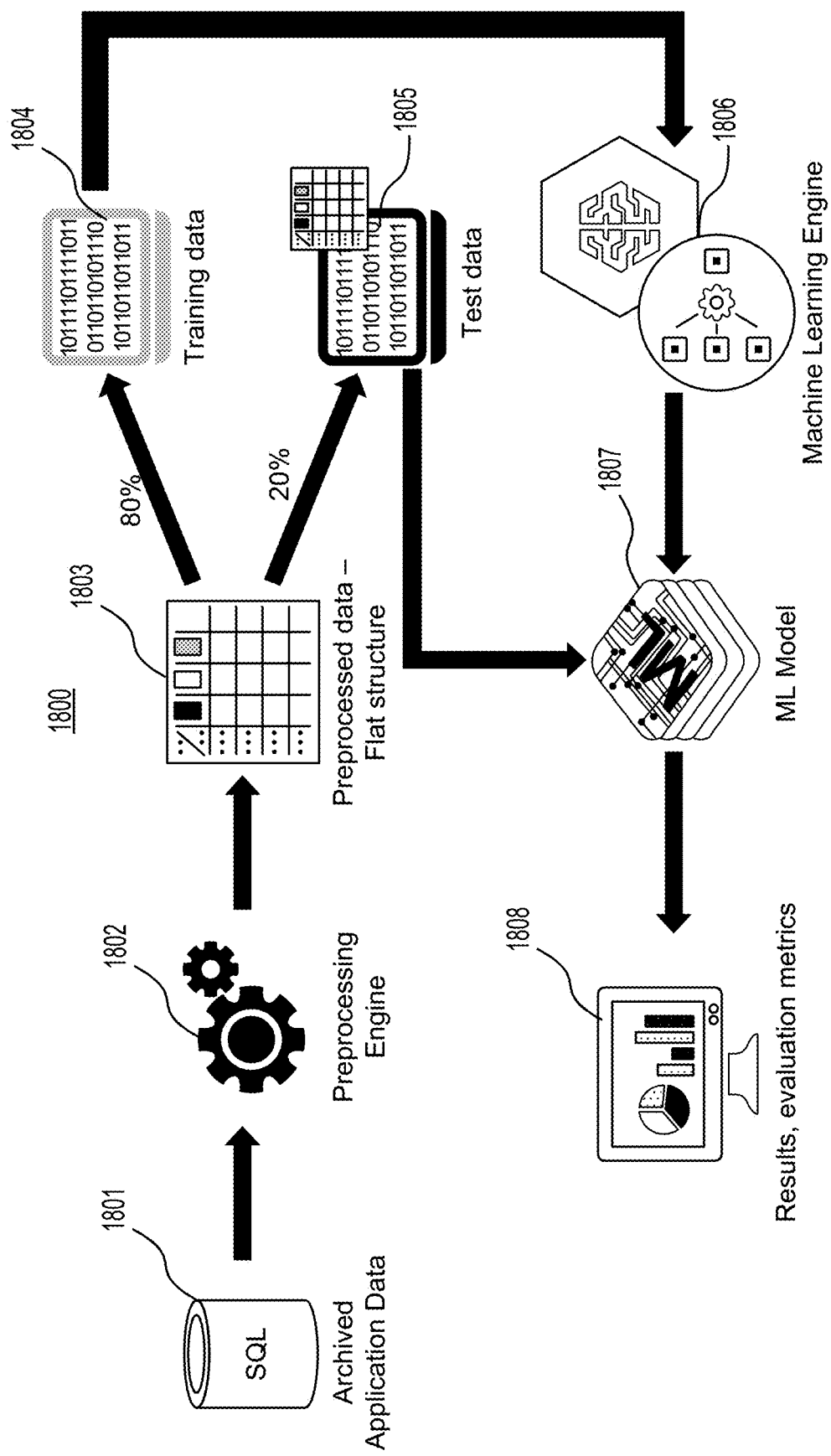
FIG. 10 is a schematic diagram of a machine learning system for determining one or more appropriate treatment facilities for patient placement, according to an example embodiment of the present disclosure.

FIG. 10 illustrates an exemplary machine learning system 1800 for determining one or more appropriate treatment facilities for patient placement, according to an exemplary embodiment of the present disclosure. The machine learning system 1800 may include archived application data 1801 that may include patient specific data and facility specific data as discussed above. The archived data may be transmitted to a preprocessing engine 1802 that may preprocess the data into a preprocessed data flat structure 1803. The preprocessed data flat structure 1803 may be separated into training data 1804 and test data 1805. The test data 1805 may be transmitted directly to the machine learning model 1807. The training data 1804 may be transmitted to a machine learning engine 1806, the machine learning engine 1806 may form, refine, and update the machine learning model 1807 based on the data provided to the machine learning engine 1806, as discussed above and in reference to FIG. 5A and FIG. 9. The machine learning model 1807 may process the data as discussed above and provide results and output evaluation metrics 1808.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented with hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

Instructions or operational steps stored by a computer-readable medium may be in the form of computer programs, program modules, or codes. As described herein, computer programs, program modules, and code based on the written description of this specification, such as those used by the processor, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A machine learning system for determining one or more appropriate treatment facilities for patient placement, comprising:
at least one memory storing instructions; and
at least one processor configured to execute the instructions to perform operations comprising:
create, for the machine learning system, at least one computer model, wherein to create comprises training the at least one computer model with training datasets comprising patient-specific training datasets and facility-specific training datasets, validating the at least one computer model with at least one validation dataset, testing the at least one computer model with at least one testing dataset, and adjusting the at least one computer model in view of a performance of the at least one computer model on the testing, wherein the training comprises performing feature selection on the at least one training dataset, wherein the feature selection comprises selecting features corresponding to patient specific data, facility specific data, environmental features, and physician data, clustering the features by computing a similarity between attributes of each of the features and attributes of patients, and assigning weights to attributes within the patient-specific training datasets and facility-specific training datasets based upon the training, validating, and testing, wherein the at least one computer model is improved based upon new data sets for a plurality of medical facilities and new patient data sets;
receive, at the machine learning system, a request from a user within a referring facility to identify at least one medical facility from the plurality of medical facilities to send a patient currently located within the referring facility, wherein the plurality of medical facilities comprises medical facilities that can receive a patient, wherein the plurality of medical facilities are in operative communication within the referring facility via the machine learning system;
access, based upon the request and from a database of the machine learning system, a patient data set comprising patient attributes and patient location metrics associated with the patient at the referring facility;
access, based upon the request and from the database of the machine learning system, a plurality of data sets for the plurality of medical facilities, the plurality of data sets comprising facility capacity metrics, facility location metrics, and facility capabilities for each of the plurality of medical facilities, wherein the plurality of data sets further comprises a list of offered services and data showing differences between facilities of the plurality of medical facilities;
extract, using the machine learning system and from the database, the patient data set and the plurality of data sets for the plurality of medical facilities, wherein the data that is extracted is based upon a role of the user;
apply, using the machine learning system, the at least one computer model to analyze the patient data set against the plurality of data sets for the plurality of medical facilities to match the patient data set with at least one of the plurality of medical facility data sets based on at least one of the patient attributes and patient location metrics and at least one of the facility capacity metrics, facility location metrics, and facility capabilities, wherein environment attributes comprising crimes and air quality are provided to the at least one computer model;
determine, based on the application of the model, one or more likelihoods of acceptance of the patient at one or more of the plurality of medical facilities and associated with each match based upon the patient data set and the plurality of data sets for the plurality of medical facilities, wherein the likelihoods of acceptance are generated by the model to assign a score to each match, wherein the likelihoods of acceptance are further based upon the environment attributes in the area of the referring facility and the one or more of the plurality of medical facilities at a time of the determining;
output, to a user interface on a display device, the at least one match with the associated likelihoods to a user device, wherein to output comprises outputting the at least one match to the user interface within a graphical user interface.

2. The machine learning system of claim 1, wherein the plurality of data sets for medical facilities further comprise prior entries of patients.

3. The machine learning system of claim 2, wherein the prior entries of patients are utilized to continuously improve the machine learning system by updating the likelihoods of acceptance.

4. The machine learning system of claim 1, wherein the patient data set further comprises patient weight, patient illness history, and patient service requested.

5. The machine learning system of claim 1, wherein the patient data set further comprises systolic blood pressure, diastolic blood pressure, heart rate, heart rhythm, respiratory rate, patient temperature, and pulse oximetry.

6. The machine learning system of claim 1, wherein the model is a neural network.

7. The machine learning system of claim 1, wherein at least two of the medical facility data sets are clustered by computing similarity between the at least two medical facility data sets and the patient data set as features to the clustering algorithms.

8. The machine learning system of claim 1, wherein at least at least one of the patient attributes and patient location metrics and at least one of the facility capacity metrics, facility location metrics, and facility capabilities are assigned weight with the amount of data that represents such cases.

9. A method for determining one or more appropriate treatment facilities for patient placement, the method comprising the following steps performed by at least one processor:
storing, in a database of a machine learning system, a plurality of data sets for a plurality of medical facilities, the plurality of data sets comprising facility capacity metrics, facility location metrics, and facility capabilities for each of the plurality of medical facilities, wherein the plurality of data sets further comprises a list of offered services and data showing differences between facilities of the plurality of medical facilities;
storing, in the database, a patient data set comprising patient attributes and patient location metrics associated with a patient currently located at a referring facility in operative communication with the plurality of medical facilities via the machine learning system, wherein the plurality of medical facilities comprises medical facilities that can receive a patient;
creating, for the machine learning system, at least one computer model, wherein to create comprises training the at least one computer model with training datasets comprising patient-specific training datasets and facility-specific training datasets, validating the at least one computer model with at least one validation dataset, testing the at least one computer model with at least one testing dataset, and adjusting the at least one computer model in view of a performance of the at least one computer model on the testing, wherein the training comprises performing feature selection on the at least one training dataset, wherein the feature selection comprises selecting features corresponding to patient specific data, facility specific data, environmental features, and physician data, clustering the features by computing a similarity between attributes of each of the features and attributes of patients, and assigning weights to attributes within the patient-specific training datasets and facility-specific training datasets based upon the training, validating, and testing, wherein the at least one computer model is improved based upon new data sets for the plurality of medical facilities and new patient data sets;

extracting, responsive to receiving a request from a user within the referring facility to identify at least one medical facility from the plurality of medical facilities to send the patient using the machine learning system and from the database, the patient data set and the plurality of data sets for the plurality of medical facilities, wherein the data that is extracted is based upon a role of the user;

applying, using the machine learning system, the at least one computer model to analyze the patient data set against the plurality of data sets for the plurality of medical facilities to match the patient data set with at least one of the plurality of medical facility data sets based on at least one of the patient attributes and patient location metrics and at least one of the facility capacity metrics, facility location metrics, and facility capabilities, wherein environment attributes comprising crimes and air quality are provided to the at least one computer model;

determining, based on the application of the model, one or more likelihoods of acceptance of the patient at one or more of the plurality of medical facilities and associated with each match based upon the patient data set and the plurality of data sets for the plurality of medical facilities, wherein the likelihoods of acceptance are generated by the model to assign a score to each match, wherein the likelihoods of acceptance are further based upon the environment attributes in the area of the referring facility and the one or more of the plurality of medical facilities at a time of the determining; and displaying, on a user interface on a display device, the at least one match with the associated likelihoods to a user device, wherein the displaying comprises outputting the at least one match to the user interface within a graphical user interface.

10. The method of claim 9, wherein the model is a neural network.

11. The method of claim 9, further comprising:
calculating the facility capacity metrics based on a total number of available beds, a total number of occupied beds, and a total number of patients.

12. The method of claim 9, wherein the displaying at least one match includes converting the at least one match to a data serialized format configured for use in a graphical user interface generator.

13. The method of claim 9, wherein the displaying at least one match includes rendering a Graphical User Interface (GUI) reflecting the at least one match.

14. The method of claim 9, wherein the patient data set further comprises patient weight, patient illness history, and patient service requested.

15. The method of claim 9, wherein the patient data set further comprises systolic blood pressure, diastolic blood pressure, heart rate, heart rhythm, respiratory rate, patient temperature, and pulse oximetry.

16. The method of claim 9, wherein the plurality of data sets for medical facilities further comprise prior entries of patients.

17. The method of claim 9, wherein the prior entries of patients are utilized to continuously improve the machine learning system by updating the likelihoods of acceptance.

* * * * *

UNITED STATES PATENT AND TRADEMARK OFFICE
CERTIFICATE OF CORRECTION

| | | |
|---|---|---|
| PATENT NO. | : 12,014,285 B2 | Page 1 of 1 |
| APPLICATION NO. | : 16/730011 | |
| DATED | : June 18, 2024 | |
| INVENTOR(S) | : Tejashree Vivek Gharat et al. | |

It is certified that error appears in the above-identified patent and that said Letters Patent is hereby corrected as shown below:

On the Title Page

Item (72) should read:
Tejashree Vivek Gharat, Pittsburgh, PA (US);
Srinivas Manoj Kamavarapu, McDonald, PA (US);
Ratna Divya Kanthi Bejjam, Bridgeville, PA (US);
Jaimin Arvindbhai Patel, Monroeville, PA (US).

Signed and Sealed this
First Day of April, 2025

Coke Morgan Stewart
*Acting Director of the United States Patent and Trademark Office*